(12) United States Patent
Gregoric et al.

(10) Patent No.: US 8,932,197 B2
(45) Date of Patent: Jan. 13, 2015

(54) VENTRICULAR PUMP COUPLING

(75) Inventors: Igor Gregoric, Houston, TX (US); Branislav Radovancevic, Houston, TX (US); Alex Y. Hsia, San Jose, CA (US)

(73) Assignee: Thoratec Corporation, Pleasanton, CA (US)

( * ) Notice: Subject to any disclaimer, the term of this patent is extended or adjusted under 35 U.S.C. 154(b) by 0 days.

(21) Appl. No.: 13/619,767

(22) Filed: Sep. 14, 2012

(65) Prior Publication Data
US 2013/0012761 A1  Jan. 10, 2013

Related U.S. Application Data

(63) Continuation of application No. 11/582,721, filed on Oct. 17, 2006, now Pat. No. 8,343,028.

(60) Provisional application No. 60/728,441, filed on Oct. 19, 2005.

(51) Int. Cl.
| A61M 1/12 | (2006.01) |
| A61M 1/10 | (2006.01) |
| A61B 17/11 | (2006.01) |
| A61B 17/00 | (2006.01) |
| A61B 18/00 | (2006.01) |

(52) U.S. Cl.
CPC ............ *A61B 17/11* (2013.01); *A61B 17/0057* (2013.01); *A61M 1/1008* (2014.02); *A61M 1/122* (2014.02); *A61B 2017/00247* (2013.01); *A61B 2018/00392* (2013.01)
USPC ........ 600/16; 604/164.03; 604/332; 604/338; 604/355; 604/107; 604/16; 604/175

(58) Field of Classification Search
USPC ...................................................... 600/16–18
See application file for complete search history.

(56) References Cited

U.S. PATENT DOCUMENTS

| 6,740,101 | B2 | 5/2004 | Houser et al. |
| 7,144,386 | B2 | 12/2006 | Korkor et al. |
| 7,306,623 | B2 | 12/2007 | Watson |
| 2003/0130668 | A1* | 7/2003 | Nieman et al. ................. 606/108 |
| 2003/0216771 | A1 | 11/2003 | Osypka et al. |
| 2004/0097993 | A1 | 5/2004 | Whayne |
| 2004/0236170 | A1 | 11/2004 | Kim |
| 2005/0043685 | A1 | 2/2005 | Schinkel-Fleitmann |
| 2005/0283193 | A1 | 12/2005 | Tullberg et al. |

OTHER PUBLICATIONS

International Search, Nov. 20, 2001, Andrulitis.
International Search Report and Written Opinion for International Application No. PCT/US06/41054 filed on Oct. 19, 2005, mailed on May 15, 2007.

* cited by examiner

*Primary Examiner* — Kennedy Schaetzle
*Assistant Examiner* — Erica Lee
(74) *Attorney, Agent, or Firm* — Stephen M. De Klerk

(57) ABSTRACT

A device and method for creating a connection with the left ventricle of a heart are provided. A seal member capable of moving between a folded position and an open position is attached to the end of a conduit. An introducer capable of moving between a first and second position allows for the expansion of the seal member into an open position. A clamp component is positioned outside of the heart to provide an axial clamping force with the wall of the heart so that a seal is created between the seal member and the wall of the heart.

10 Claims, 14 Drawing Sheets

VENTRICULAR PUMP COUPLING

CROSS-REFERENCE TO RELATED APPLICATIONS

The is a continuation of prior U.S. patent application Ser. No. 11/582,721, filed on Oct. 17, 2006 U.S. Pat. No. 8,343,028, which claims priority from U.S. Provisional Patent Application No. 60/728,441, filed on Oct. 19, 2005, which are incorporated herein by reference in their entirety.

BACKGROUND OF THE INVENTION

1). Field of the Invention

This invention relates to a ventricular pump coupling device that provides a tight seal between the left ventricle of a heart and a conduit.

2). Discussion of Related Art

Ventricular assist devices are mechanical devices that are used to assist or replace cardiac functions. These devices are capable of partially or completely replacing the functioning of a failing heart.

The heart is located in the thoracic cavity and is generally partitioned into the left and right half. Each half consists of an atrium and a ventricle. The ventricles are described as the left ventricle or right ventricle. Likewise, the atria are described as the left atrium and right atrium. The wall of each ventricle is comprised of three layers of tissue: the endocardium, the myocardium, and the epicardium. The endocardium is the tissue on the inner layer of the ventricle, while the epicardium is the tissue on the outer layer of the ventricle functioning as a protective layer. The myocardium is essentially the middle layer of tissue between the endocardium and epicardium.

In order to implement a ventricular assist device, a connection must be made to the left ventricle of the heart through the three layers of tissue, to enable blood flow to the ventricle cavity.

The connection to the left ventricle can be achieved through the use of a connection device. In one example, a connection such as screw-type connectors can be used, where the user must core a hole into the heart and place sutures around the hole to insert a cuff to be secured by suturing. A tube is then inserted into the sutured cuff and a tie-down may be required around the outer diameter of the cuff to hold the tube in place.

One of the problems with this method is that the screw-type procedure is work-intensive and requires extensive suturing. Even when a cuff is sutured in place, there is no guarantee that the connection between the tube and the cuff is adequately sealed and reliable.

Furthermore, the screw-type procedure damages the tissue layers of the left ventricle and may interfere with the contraction and functioning of the left ventricle. The procedure also requires that a portion of the myocardium be removed, which may affect the functioning of the heart.

SUMMARY OF THE INVENTION

The invention provides a device for creating a sealed connection at an opening in a wall of a heart, comprising a conduit, having an end, a seal member attached to the end of the conduit and capable of moving between a folded position and an open position to expand the seal member so that the seal member has a cross-dimension that is larger than a cross-dimension of the opening in the wall of the heart, and a clamp component to be positioned outside of the heart, the seal member and the clamp component being movable relative to one another to produce an axial clamping force with the wall of the heart between the clamp component and the seal member so that a seal is created between the seal member and the wall of the heart.

The seal member preferably has a ribbed surface to engage the wall of the heart.

The device may further comprise at least one expansion spring within the seal member to expand the seal member within the heart, wherein the seal member may be molded silicone having a biocompatible coating.

The device may further comprise an introducer being secured for movement between first and second positions relative to the conduit, in the first position, the introducer maintaining the seal member in the folded position to allow for insertion of the seal member through the opening into the heart and, in the second position, the introducer allowing for expansion of the seal member so that the seal member has a cross-dimension that is larger than a cross-dimension of the opening in the wall of the heart.

The introducer may have retractable fingers, and may be rotatable into a locked position to prevent movement of the introducer in the axial direction relative to the conduit. The introducer may also be tapered on one end and may be slideably engaged with a stop on the seal member to prevent movement of the introducer in the axial direction relative to the conduit.

The introducer may be selected from at least one of nitinol or stainless steel.

The introducer may passively allow the seal member to expand to an open position, and may expand under a spring force.

The device may further comprise a wire frame, plastic deformation of at least a portion of the wire frame causing expansion of the seal member. Movement of the conduit relative to the wire frame may cause deformation of the portion of the wire frame.

The clamp component may have an epicardial seal piece having an inner and outer diameter to engage the wall of the heart, and may have a flange being attached to the epicardial seal piece. The clamp component may also have a mounting piece being attached to the flange, and a locking mechanism attached to the mounting piece.

The locking mechanism may have a plurality of teeth to close the locking mechanism, the locking mechanism engaging the introducer and the flange to produce the axial clamping force. The locking mechanism may be polytetrafluoroethylene.

The flange may have an outer diameter and an inner diameter having a plurality of teeth.

The invention further provides a method for creating a sealed connection at an opening in a wall of a heart, including inserting an introducer and a seal member, in a folded position, through an opening in the wall of the heart, expanding the seal member to an open position within the heart so that the seal member has a cross-dimension that is larger than a cross-dimension of the opening in the wall of the heart, and moving a clamp component relative to the seal member to create an axial clamping force with the wall of the heart between the clamp component and the seal member so that a seal is created between the seal member and the wall of the heart.

BRIEF DESCRIPTION OF THE DRAWINGS

The invention is described by way of examples with reference to the accompanying drawings, wherein.

DETAILED DESCRIPTION OF THE INVENTION

A connector is provided, being connectable to an opening in the wall of the left ventricle of the heart. The connector has a conduit, a seal member attached to an end of the conduit and capable of moving between a folded position and an open position to expand the seal member so that the seal member has a cross-dimension that is larger than a cross-dimension of the opening in the wall of the heart, and a clamp component to be positioned outside of the heart. The seal member and the clamp component are movable relative to one another to produce an axial clamping force with the wall of the heart between the clamp component and the seal member so that a seal is created between the seal member and the wall of the heart.

The invention also provides a pump having an inlet and outlet, a motor for driving the pump, an energy source for operating the motor, and an outflow tube having a first end and a second end, wherein the first end is connected to the outlet of the pump and the second end is connectable to a blood vessel.

Figure 1:
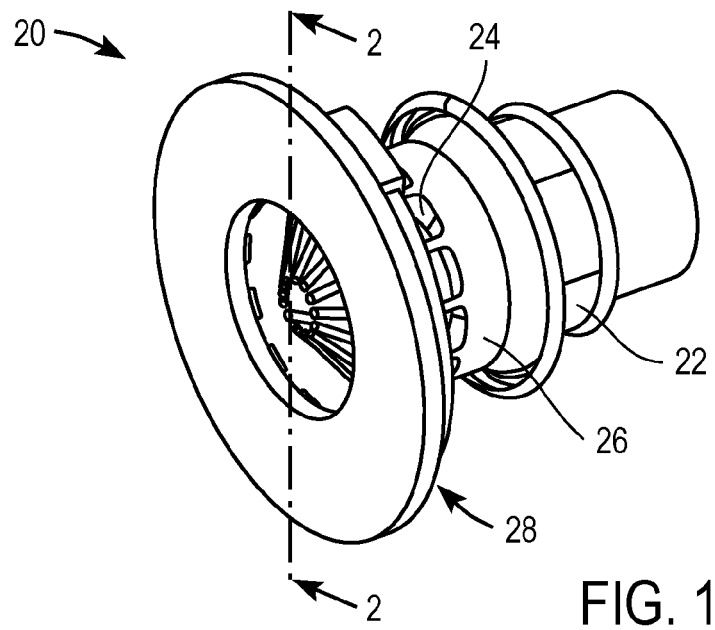
FIG. 1 is an perspective view of the ventricular pump coupling assembly, according to one embodiment of the invention.
Figure 2:
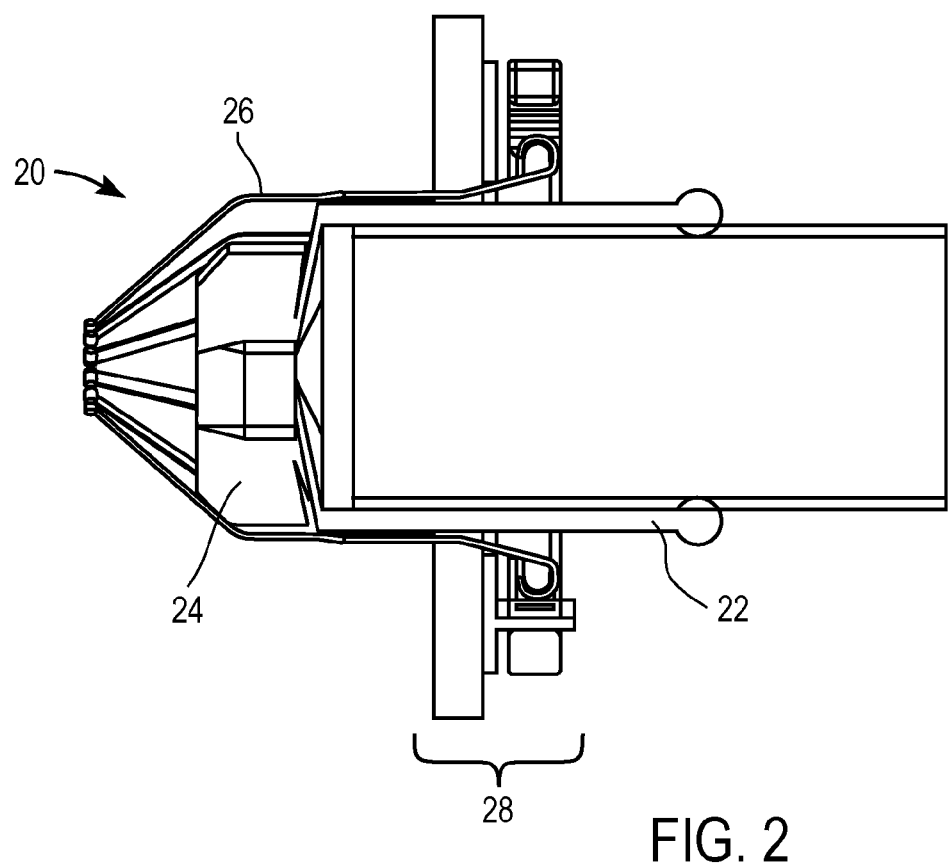
FIG. 2 is a cross-sectional side view taken on 2-2 of FIG. 1.

FIGS. 1 and 2 of the accompanying drawings illustrate a ventricular pump coupling 20, according to one embodiment of the invention, including a sleeve 22, a seal member 24, an introducer 26, and a clamp component 28, with the seal member 24 in a folded position.

The components and assembly of the ventricular pump coupling 20 are first described with respect to FIGS. 3 to 9, whereafter its functioning is described.

Figure 3:
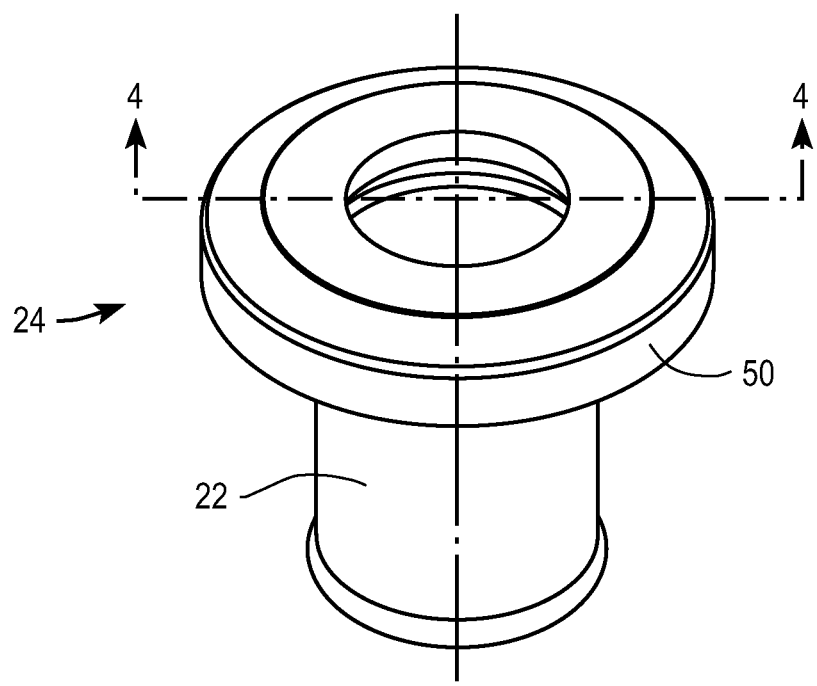
FIG. 3 is an perspective view of a seal member forming part of the ventricular pump coupling.
Figure 4:
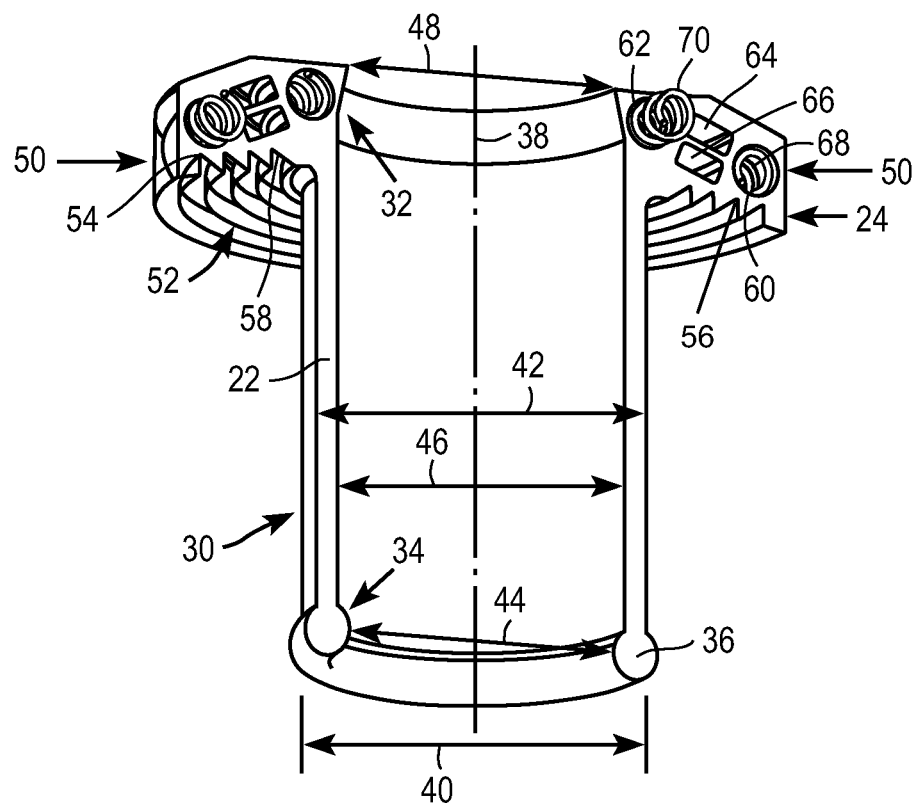
FIG. 4 is a cross-sectional front view taken on 4-4 of FIG. 3.

FIGS. 3 and 4 illustrate the sleeve 22 and the seal member 24 of the ventricular pump coupling 20. The sleeve 22 has a center portion 30, a first end 32 where the seal member 24 is attached, a second end 34 having a circumferential stop lip 36, and a central axis 38 substantially parallel to the center portion 30 of the sleeve 22. An outer diameter 40 of the circumferential stop lip 36 is greater than an outer diameter 42 of the center portion 30. Furthermore, an inner diameter 44 of the circumferential stop lip 36 is less than an inner diameter 46 of the center portion 30. An inner diameter 48 of the first end 32 of the sleeve 22 is slightly less than the inner diameter 46 of the center portion 30.

The seal member 24 is attached to the first end 32 of the sleeve 22. The seal member 24 has a similar inner diameter to the first end 32 of the sleeve 22. The seal member 24 also has an outer diameter 50, and a central axis 38 that is coaxial with the central axis 38 of the sleeve 22. The seal member 24 and sleeve 22 are typically formed together from the same material in a single molding operation. The seal member 24 and sleeve 22 can be made of silicone or any other biocompatible material. A biocompatible coating can also be applied to the outer surface of the seal member 24.

Referring to FIG. 4, the seal member 24 has a ribbed surface 52 facing the second end 34 of the sleeve 22 for securing the seal member 24 position within a heart. The ribbed surface 52 of the seal member 24 has four circumferential grooves 54 forming the ribs. An individual rib has a first surface 56 substantially parallel to the central axis of the seal member and a second surface 58 angled relative to the central axis 38 of the seal member 24.

Furthermore, as shown in FIG. 4, the seal member 24 contains a first circumferential bore hole 60 within the seal member 24 in close proximity to the outer diameter 50 of the seal member 24, and a second circumferential bore hole 62 within the seal member 24 in close proximity to the inner diameter 48 of the seal member 24. First and second rectangular circumferential bores 64 and 66 are disposed between the first and second bore holes 60 and 62. The rectangular circumferential bores 64 and 66 are spaced apart from each other in a direction of the central axis 38. First and second circumferential coil springs 68 and 70 are disposed within each of the first and second circumferential bore holes 60 and 62 to actively expand the seal member 24 from a folded position to an open position.

Figure 5:
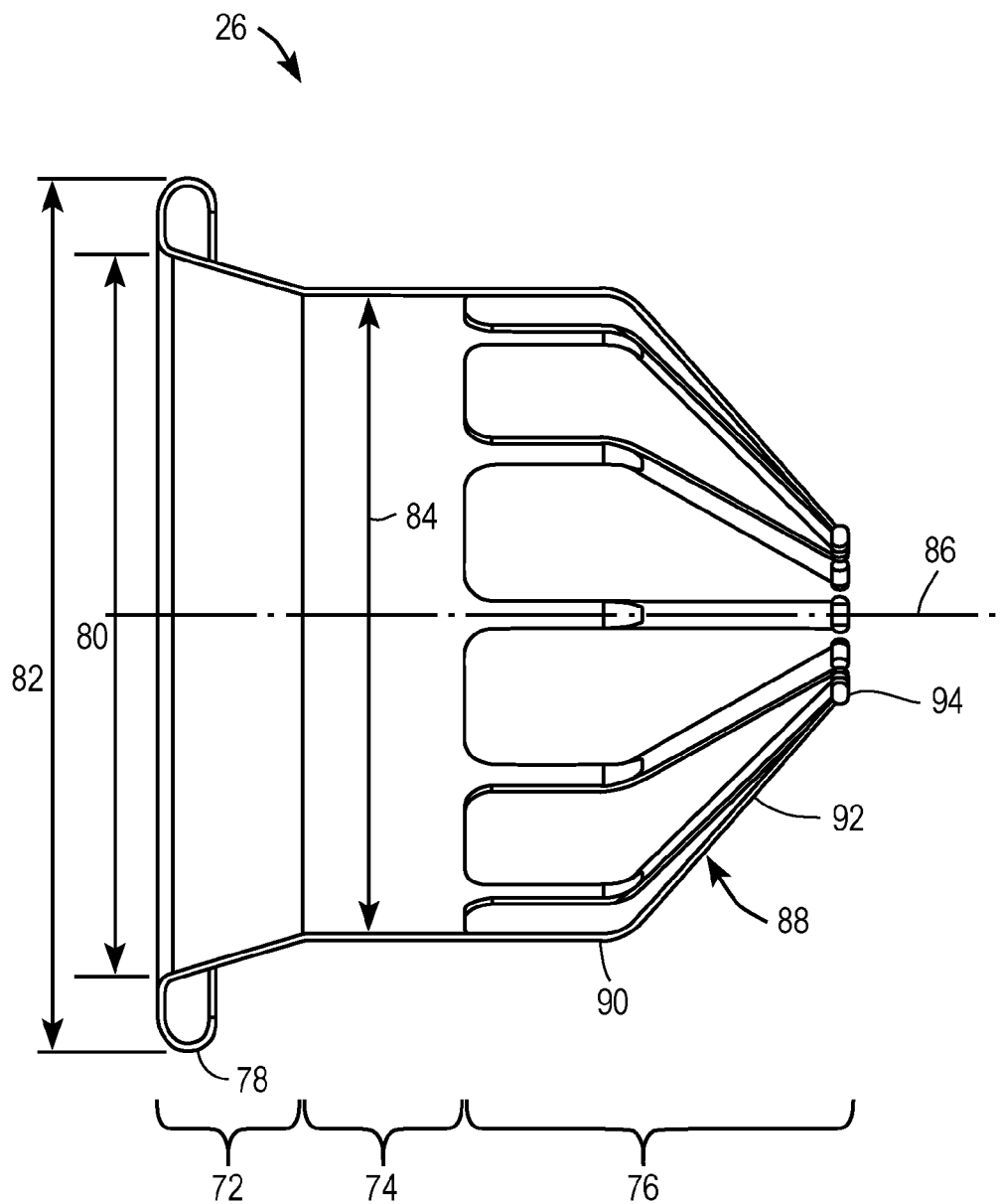
FIG. 5 is a cross-sectional side view of an introducer forming part of the ventricular pump coupling.

As shown in FIG. 5, the introducer 26 is shown in an insertion position, the introducer 26 being made from laser-cut nitinol or stainless steel. The introducer 26 has a grip end 72, center portion 74, and an insertion end 76. The grip end 72 of the introducer 26 has a flared circumferential lip portion 78 having an inner diameter 80 and outer diameter 82. The lip portion 78 extends in a circumferentially radial direction perpendicular to a central axis 86 of the introducer 26, forming the outer diameter 82 of the grip end 72. The lip portion 78 curls slightly back in an inward direction toward the central axis 86 away from the outer diameter 82 of the grip end 72. The grip end 72 tapers inwardly from the lip portion 78 toward the center portion 74, having a constant inner diameter 84 less than the inner diameter 80 of the lip portion 78. The center portion 74 of the introducer 26 connects the grip end 72 to the insertion end 76.

The insertion end 76 is comprised of a plurality of inwardly bent retractable fingers 88 extending from the center portion 74 of the introducer 26 in an axial direction. Each finger has a base segment 90, an intermediate segment 92, and a tip 94. The base segment 90 of a finger 88 is attached to the center portion 74 of the introducer 26 and is substantially parallel with the center portion 74. The intermediate segment 92 of a finger 88 is connected to the base segment 90 of the finger 88 at a first angle relative to the base segment 90 and center portion 74 of the introducer 26. The tip 94 of a finger 88 having a diameter and circular cross-section is positioned at an end of the intermediate segment 92. The plurality of fingers 88 and tips 94 in the aggregate form a circular arrangement having a diameter smaller than the inner diameter 84 of the center portion 74 of the introducer 26.

Figure 6:
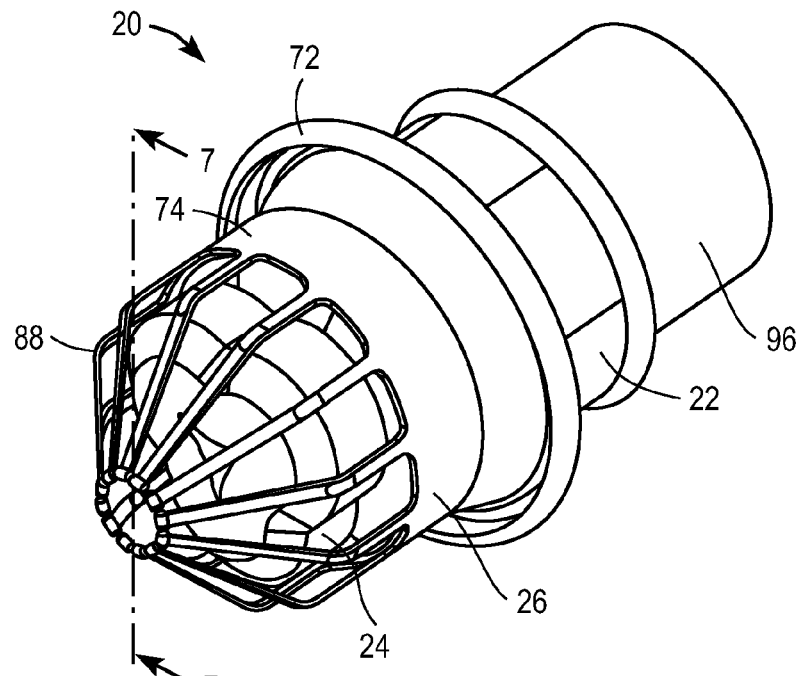
FIG. 6 is an perspective view of the seal member, a sleeve, the introducer, and a conduit forming a partial assembly of the ventricular pump coupling.
Figure 7:
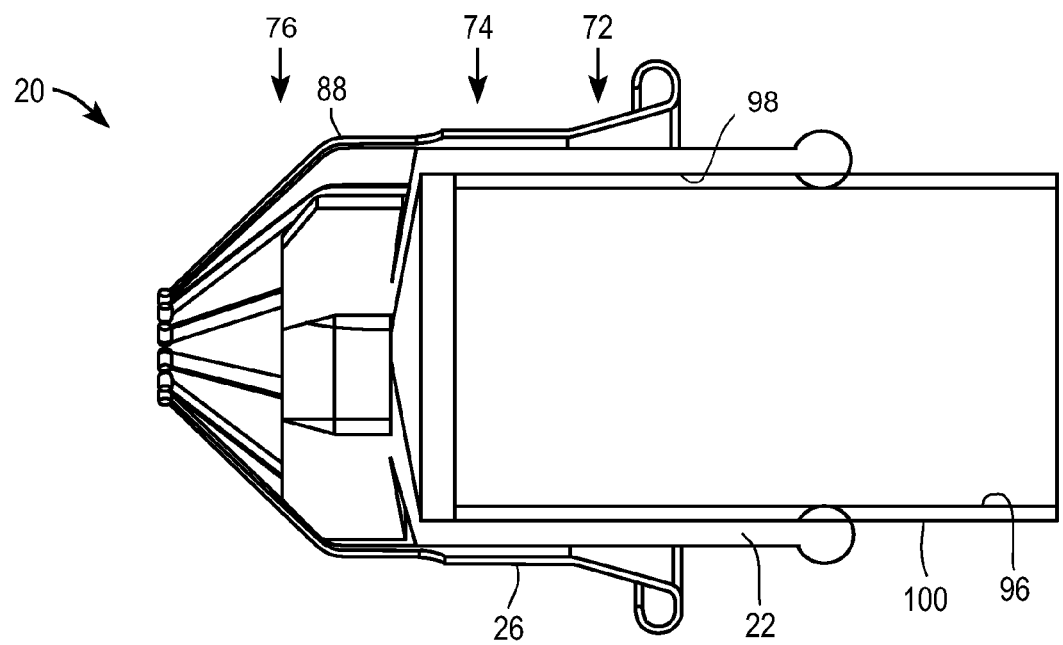
FIG. 7 is a cross-sectional side view taken on 7-7 of FIG. 6.

As shown in FIG. 6, during assembly, the sleeve 22 of the seal member 24 is engaged with a conduit 96, made of titanium or any other relatively rigid material. As further shown in FIG. 7, the conduit 96 is inserted into the sleeve 22 in a co-axial relationship so that an inner wall 98 of the sleeve 22 and an outer wall 100 of the conduit 96 are engaged. The circumferential stop lip 36 engages the outer wall 100 of the conduit 96, through a friction fit, to prevent the sleeve 22 from sliding off the conduit 96.

The introducer 26 is placed over the folded seal member 24 and sleeve 22 so that the introducer 26 is coaxial with the folded seal member 24 and sleeve 22. The grip end 72, center portion 74, and part of the fingers 88 surround the sleeve 22 of the seal member 24. The fingers 88 of the insertion end 76 of the introducer 26 engage the folded seal member 24 to prevent the circumferential coil springs 68 and 70 within the seal member 24 from expanding the folded seal member 24.

Figure 8:
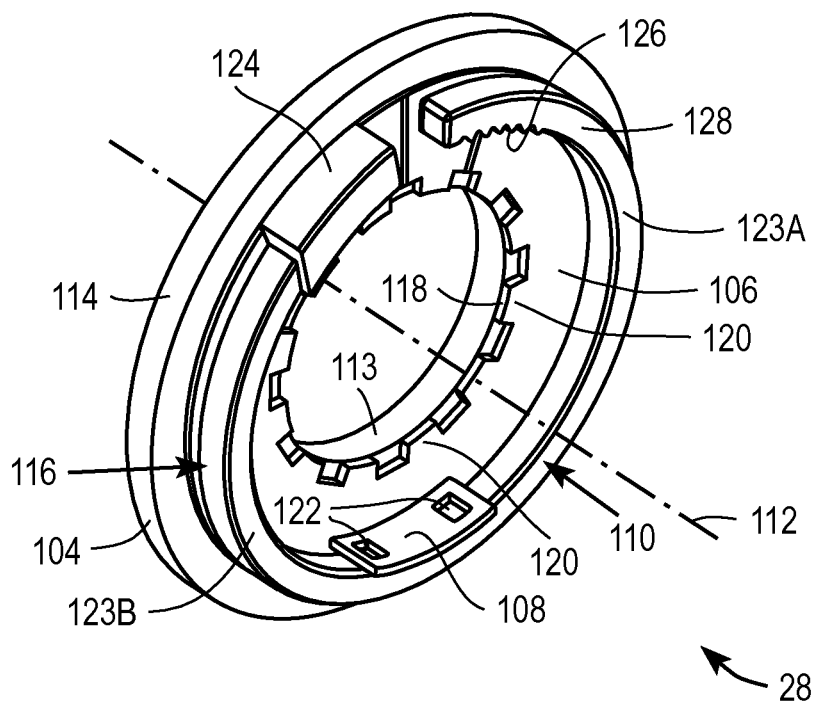
FIG. 8 is an perspective view of a clamp component forming part of the ventricular pump coupling, wherein a locking mechanism is in an open position.

Referring to FIG. 8, the clamp component 28 is shown having an epicardial seal piece 104, a flange 106, a mounting piece 108, and a locking mechanism 110 all having a coaxial central axis 112 relative to one another. The epicardial seal piece 104 has an inner diameter 113 and an outer diameter 114 and is a polytetrafluoroethylene material or other biocompatible material suitable for suture. The flange 106 is made of stainless steel, or any other preferable material, and is attached to the epicardial seal piece 104 having an outer diameter 116 and an inner diameter 118 with a plurality of flange teeth 120. The inner diameter 118 of the flange 106 is substantially similar to the inner diameter 113 of the epicardial seal piece 104, so that top portions of the flange teeth 120 are substantially aligned with the inner diameter 113 of the epicardial seal piece 104.

The rectangular-shaped mounting piece 108 is attached to the flange 106 by thermobonding or any other mechanical means, or may be bent out of a plane of the flange 106. The rectangular-shaped mounting piece 108 has two notches 122 and is slightly curved for easily attaching the locking mechanism 110.

The locking mechanism 110 has a ratchet mechanism 124, rack teeth 126, and a lock body 128. The locking mechanism 110 can be polytetrafluoroethylene or any other suitable material. The lock body 128 has a circular shape with a rectangular cross-section. The lock body 128 has the ratchet mechanism 124 on one end 123B and rack teeth 126 on the other end 123A. The rack teeth 126 are located on an inner circumferential surface of the lock body 128, with rack teeth 126 extending toward the central axis 112 of the clamp component 102.

Figure 9:
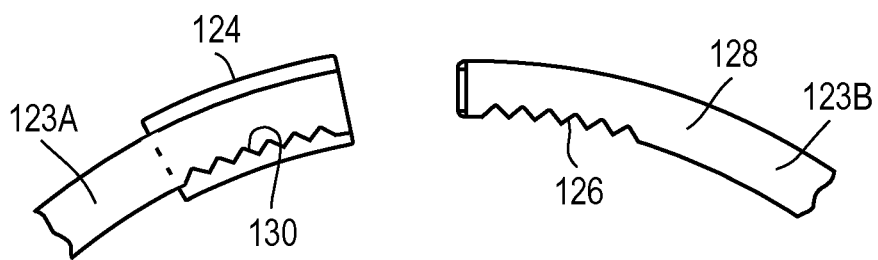
FIG. 9 illustrates a ratchet mechanism and rack teeth of the locking mechanism in an open position.

As shown in FIG. 9, the ratchet mechanism 124 has ratchet teeth 130 facing radially outward from the central axis 112 to engage the rack teeth 126 when the rack teeth 126 are inserted into the ratchet mechanism 124. A force is provided to maintain the rack teeth 126 and the ratchet teeth 130 engaged with one another to provide a locking force.

When the locking mechanism 110 is in a closed position with the rack teeth 126 engaging the ratchet mechanism 124, the diameter of the lock body 128 can be decreased by further movement of the rack teeth 126 into the ratchet mechanism 124. The decrease in diameter of the lock body 128 provides a clamping force on objects in contact with the lock body 128.

Referring again to FIG. 2, the fully assembled coupling 20 has the seal member 24 and sleeve 22 attached to the end of the conduit 96, and the introducer 26 is located in a first position relative to the conduit 96, wherein the introducer 26 is placed over the seal member 24 to maintain the seal member 24 in a folded position. The clamp component 28 is then placed over the introducer 26 so that the clamp component 28, seal member 24, sleeve 22, and introducer 26 are coaxially arranged having a common central axis.

Figure 10:
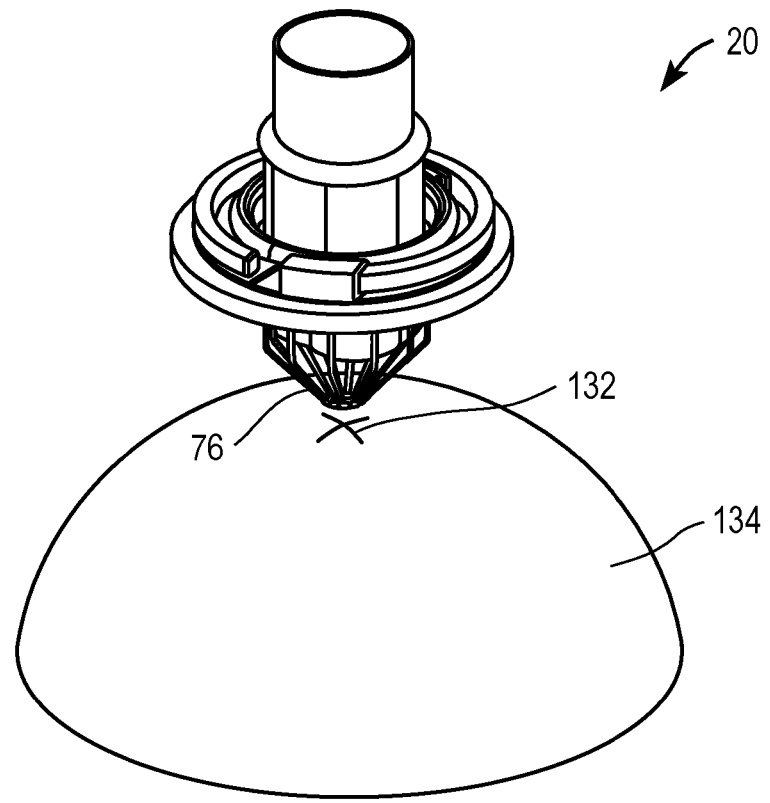
FIG. 10 is a perspective view of the ventricular pump coupling assembly before insertion into an incision in the heart.

In use, referring to FIG. 10, an incision 132 is made in the wall of the left ventricle of the heart 134 before insertion of the fully assembled coupling connector 20. The insertion end 76 of the introducer 26 is aligned with the incision 132 made in the wall of the heart 134 prior to insertion into the heart 134.

Figure 11:
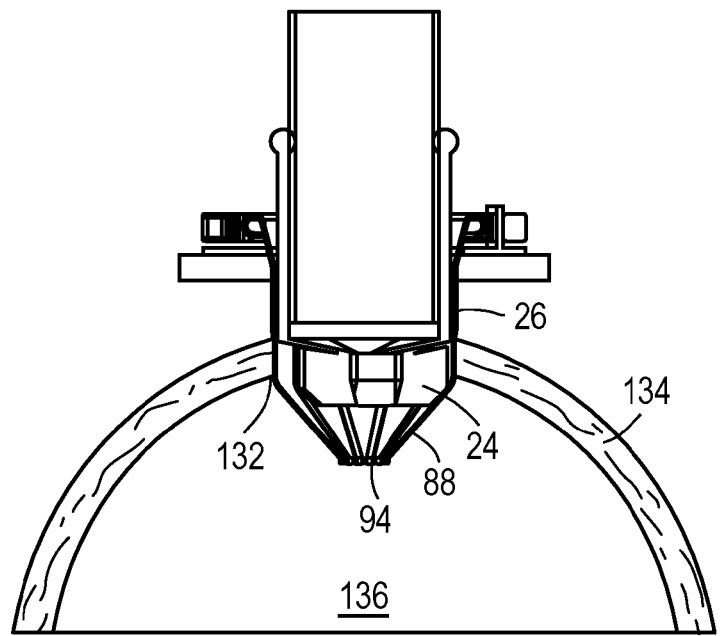
FIG. 11 is a cross-sectional side view of the ventricular pump coupling assembly after insertion into an incision in the heart, with the introducer in a first position.

As shown in FIG. 11, the tips 94 of the fingers 88 of the introducer 26 engage the incision 132 made in the heart 134, allowing for a majority of the fingers 88 and the folded seal member 24 to enter a left ventricle 136 upon a forward insertion movement.

Figure 12:
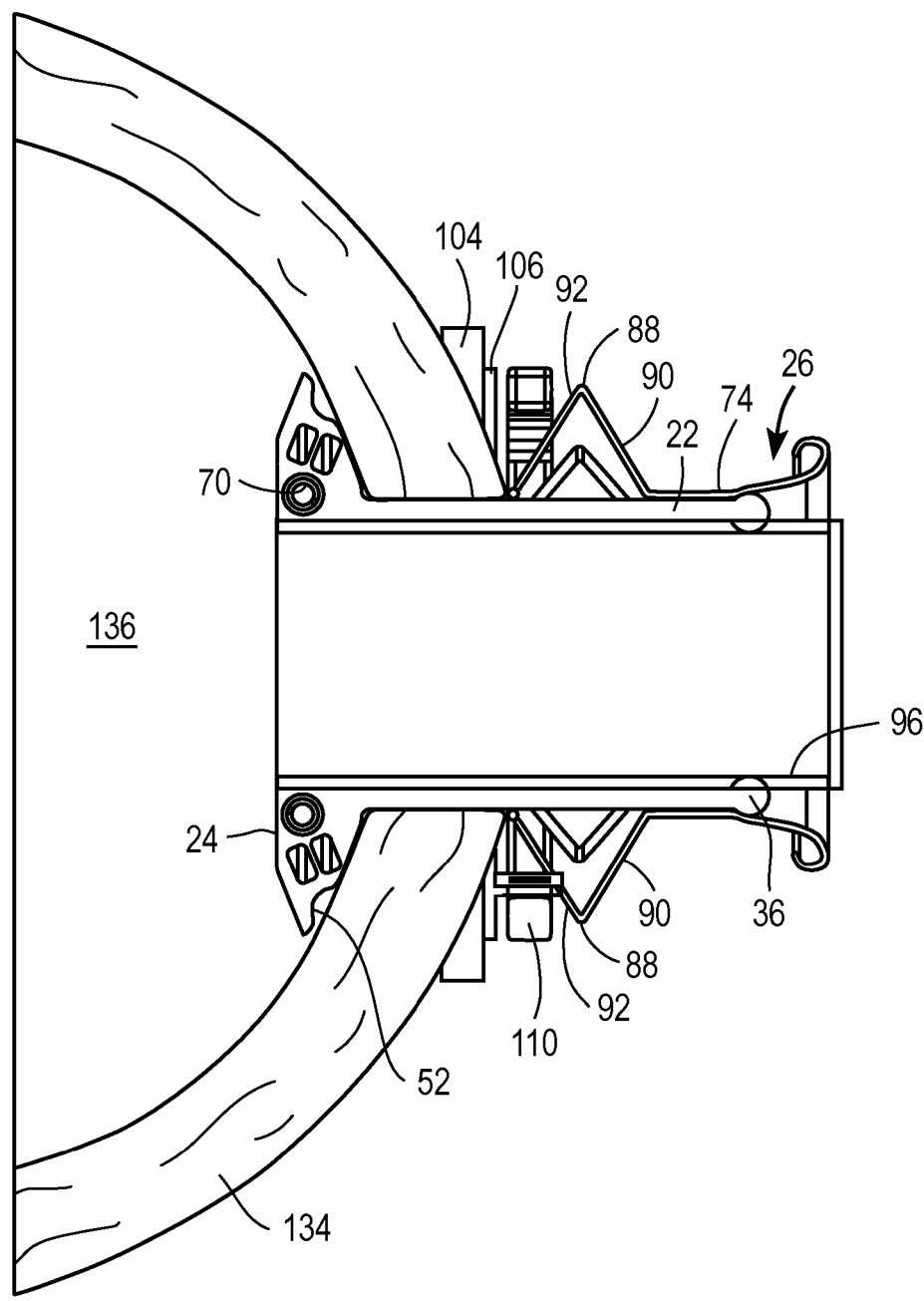
FIG. 12 is a cross-sectional side view similar to FIG. 11, illustrating the ventricular pump coupling assembly wherein the introducer is moved to a second position and the seal member is in an open position.

A shown in FIG. 12, the introducer 26 is withdrawn to a second position in an axial direction away from the heart 134 and relative to the sleeve 22 and the conduit 96. The second position can be reached by a user applying an axial force to the grip end 72 of the introducer 26 to slide the introducer 26 to the second position until the introducer 26 engages the stop lip 36. Further movement of the introducer 26 is prevented by the stop lip 36, and the rigidity of the conduit that prevents inward deflection of the stop lip 36.

As the introducer 26 is moved to the second position, the fingers 88 release the folded seal member 24, allowing the coil springs 68 and 70 embedded in the seal member 24 to expand from a folded position to an open position within the heart 134. The rib surface 52 of the seal member 24 engages an inner surface of the wall of the heart 134 upon expansion. The fingers 88 slide on the outer surface of the sleeve 22 of the seal member 24 to a final bent position. The fingers 88 then have a second angle between the intermediate segments 92 and base segments 90 of the fingers 88 that is less than the first angle between the intermediate segments 92 and base segments 90 in the first position of the introducer 26. Moreover, in the second position, the base segments 90 of the fingers 88 are no longer substantially parallel with the center portion 74 of the introducer 26. The base segments 90 of the fingers 88 now have an angle relative to the center portion 74 of the introducer 26.

The fingers 88 form a triangular opening with the surface of the sleeve 22. The tips 94 are withdrawn from the left ventricle 136 of the heart 134, and are positioned between the flange 106 and the locking mechanism 110. The intermediate segments 92 extend at an angle relative to the central axis 86 of the introducer 26 from the tips 94 to a point away from the surface of the seal member sleeve 22, where the intermediate segment 92 connects to the base segment 90. The intermediate segments 92 also extend from the tips 94 in a direction away from the heart 134 at an angle relative to the central axis 86 of the introducer 26. A portion of each intermediate segment 92 is located under the locking mechanism 110 for engagement with the locking mechanism 110 when it is closed.

As mentioned, the introducer 26 engages the stop lip 36 of the seal member 34 and sleeve 22 to prevent the introducer 26 from moving any further in the axial direction. The introducer 26 can also be rotated to a locked position to prevent axial movement when the introducer 26 has reached the second position.

Figure 13:
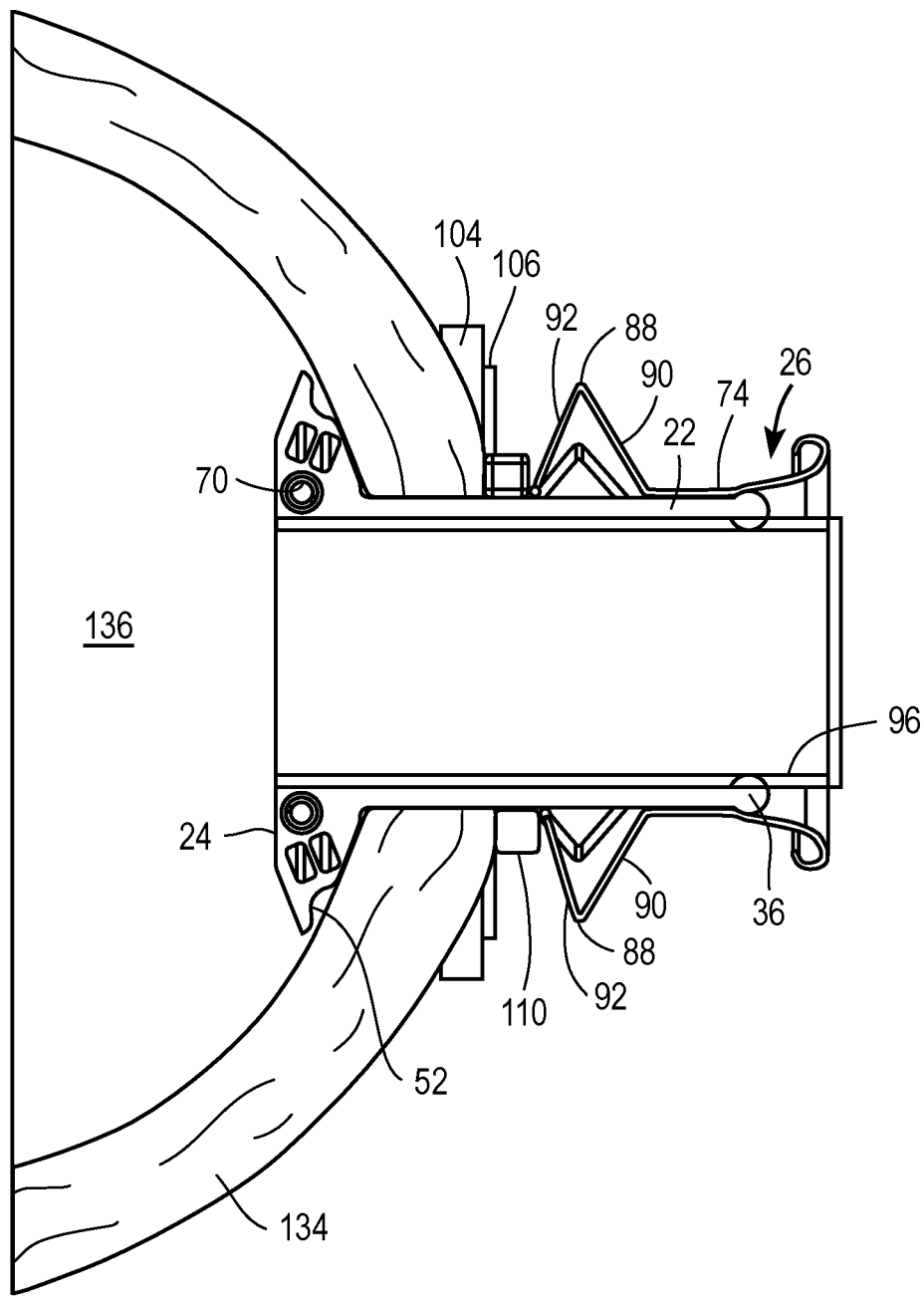
FIG. 13 is a cross-sectional side view similar to FIG. 12, illustrating the ventricular pump coupling assembly wherein the locking mechanism is closed and an axial force is produced.

As shown in FIG. 13, after the introducer 26 has reached the second position, the locking mechanism 110 is then closed by inserting the rack teeth 126 into the ratchet mechanism 124 to decrease the diameter of the lock body 128. As the diameter of the lock body 128 decreases, the lock body 128 engages an angled top surface of the intermediate segments 92 to produce an axial force on the flange 106 and epicardial seal piece 104 in a direction of the heart 134. The axial force causes the wall of the left ventricle of the heart 134 to be clamped between the epicardial seal piece 104, located outside of the heart 134, and the ribbed surface 52 of the seal member 24, located inside of the left ventricle 136.

Figure 14:
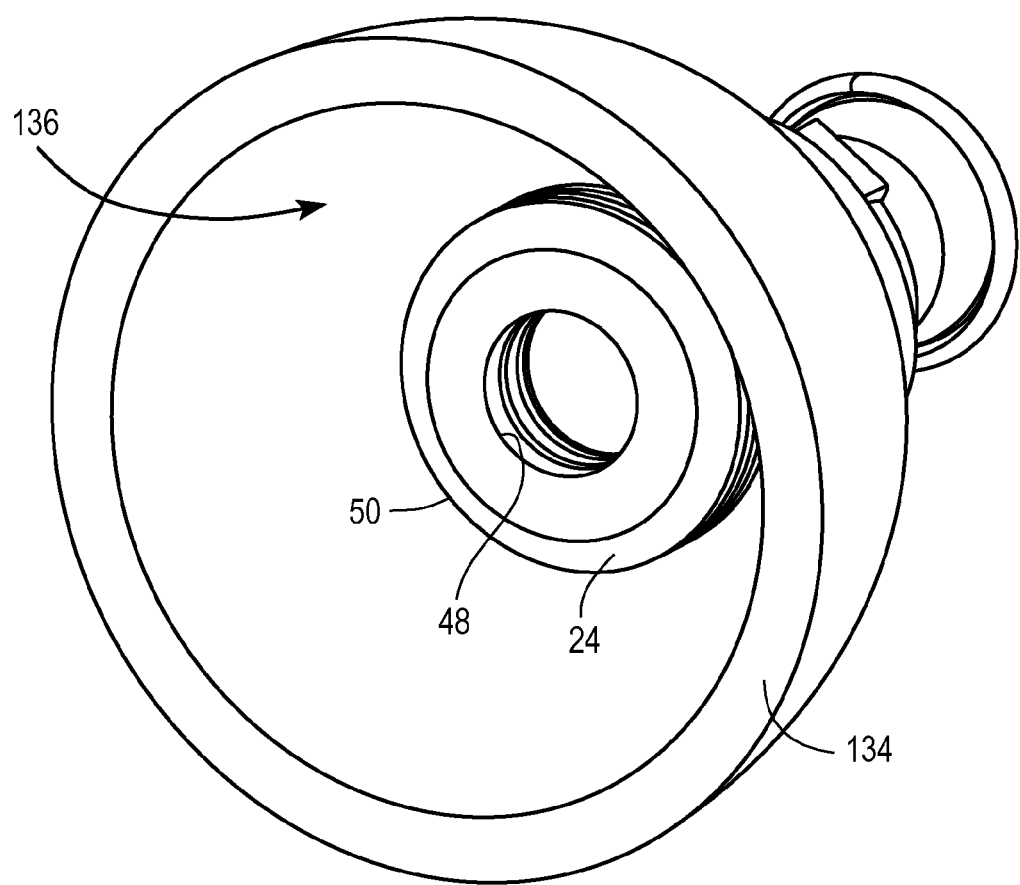
FIG. 14 is a perspective view of the seal member in an open position within the left ventricle cavity of the heart.

Referring to FIG. 14, the seal member 24 is in an open position within the left ventricle 136. The inner diameter 48 of the seal member 24 provides an opening for blood to flow into the left ventricle 136. The outer diameter 50 of the seal member 24 is greater than a cross-diameter of the incision 132 to ensure a tight seal.

Figure 15A:
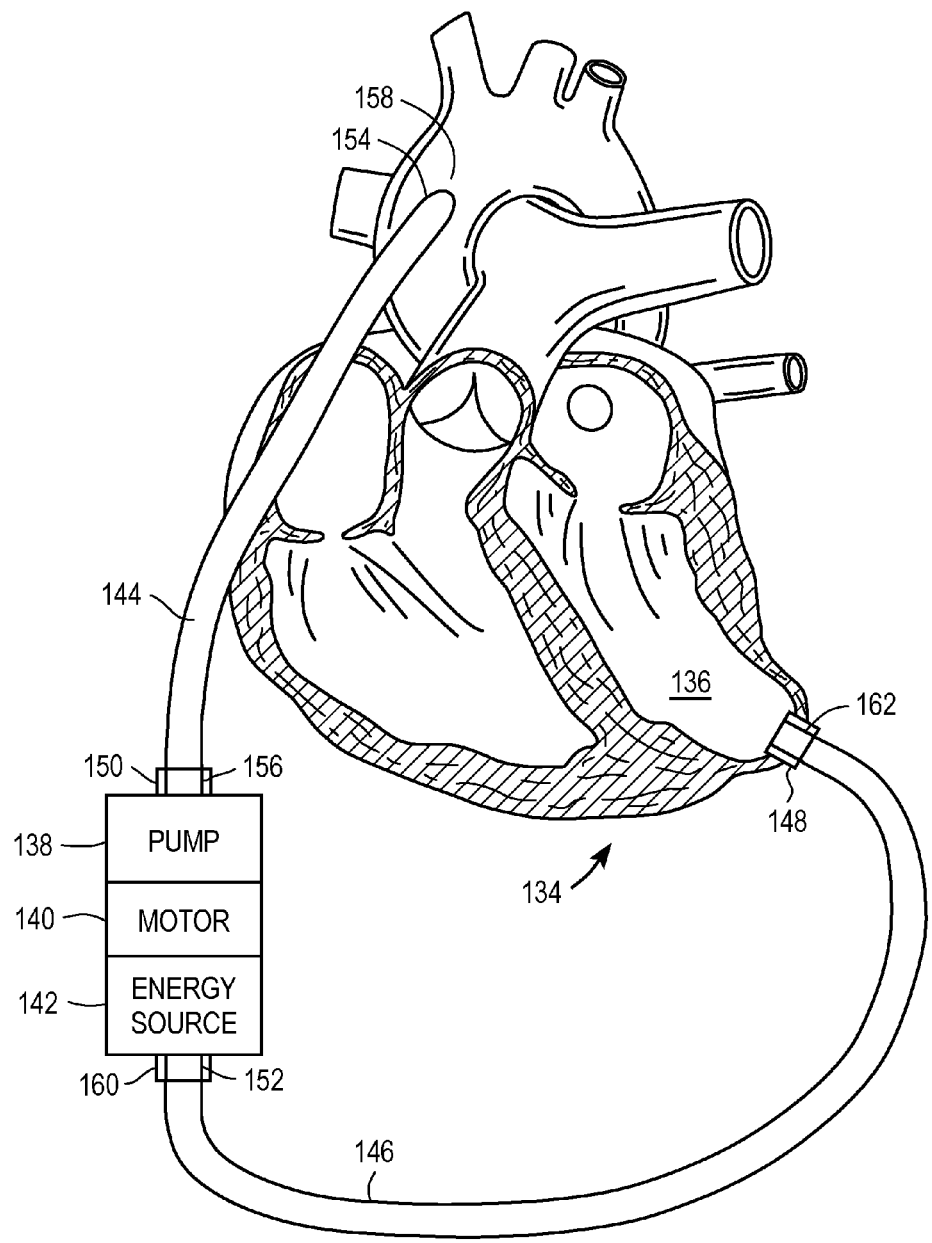
FIGS. 15A and 15B are system drawings illustrating a device assisting the left ventricle of the heart.
Figure 15B:
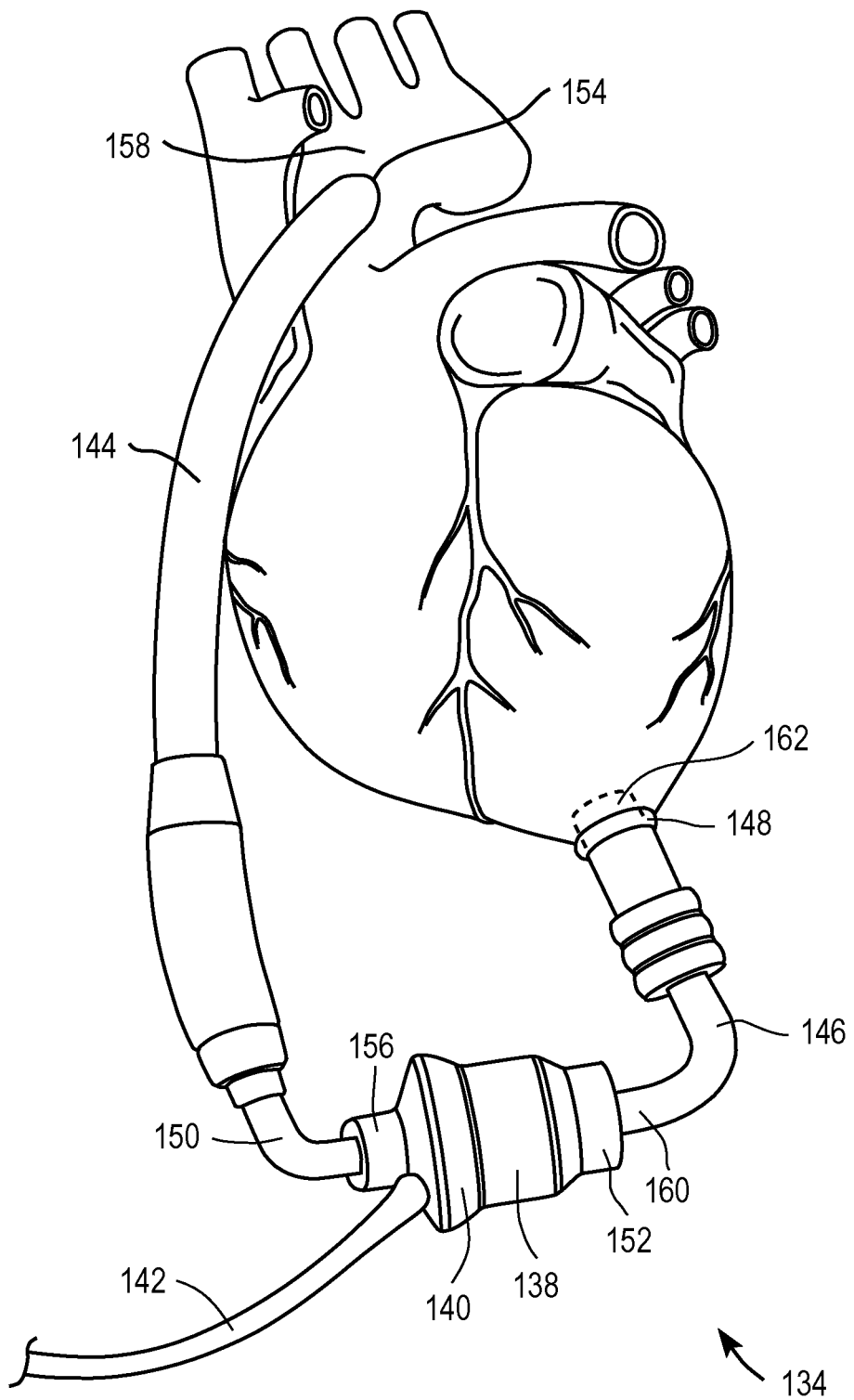

As shown in FIGS. 15A and 15B, a pump 138, motor 140, energy source 142, inflow tube 146, outflow tube 144, and connector 148 are provided for assisting a left ventricle of the heart 134. The pump 138 has an inlet 152 and an outlet 150, and the motor 140 is provided for driving the pump 138. The energy source 142 is also provided to operate the motor 140. The inflow tube 146 with a first end 162 and second end 160 are connected to the connector 148 to receive blood through the first end 162. The second end 160 of the inflow tube 146 is connected to the inlet 152 of the pump 138 to allow blood to flow to the pump 138 from the left ventricle 136.

The outflow tube 144 also has a first end 156 and a second end 154. The first end 156 of the outflow tube 144 is connected to the outlet 156 of the pump 138, and the second end 154 of the outflow tube 144 is attached to the aorta 158 (the blood vessel leading out of the left ventricle 136). The outflow tube 144 receives blood from the outlet 150 of the pump 138 and delivers it to the aorta 158.

Figure 16:
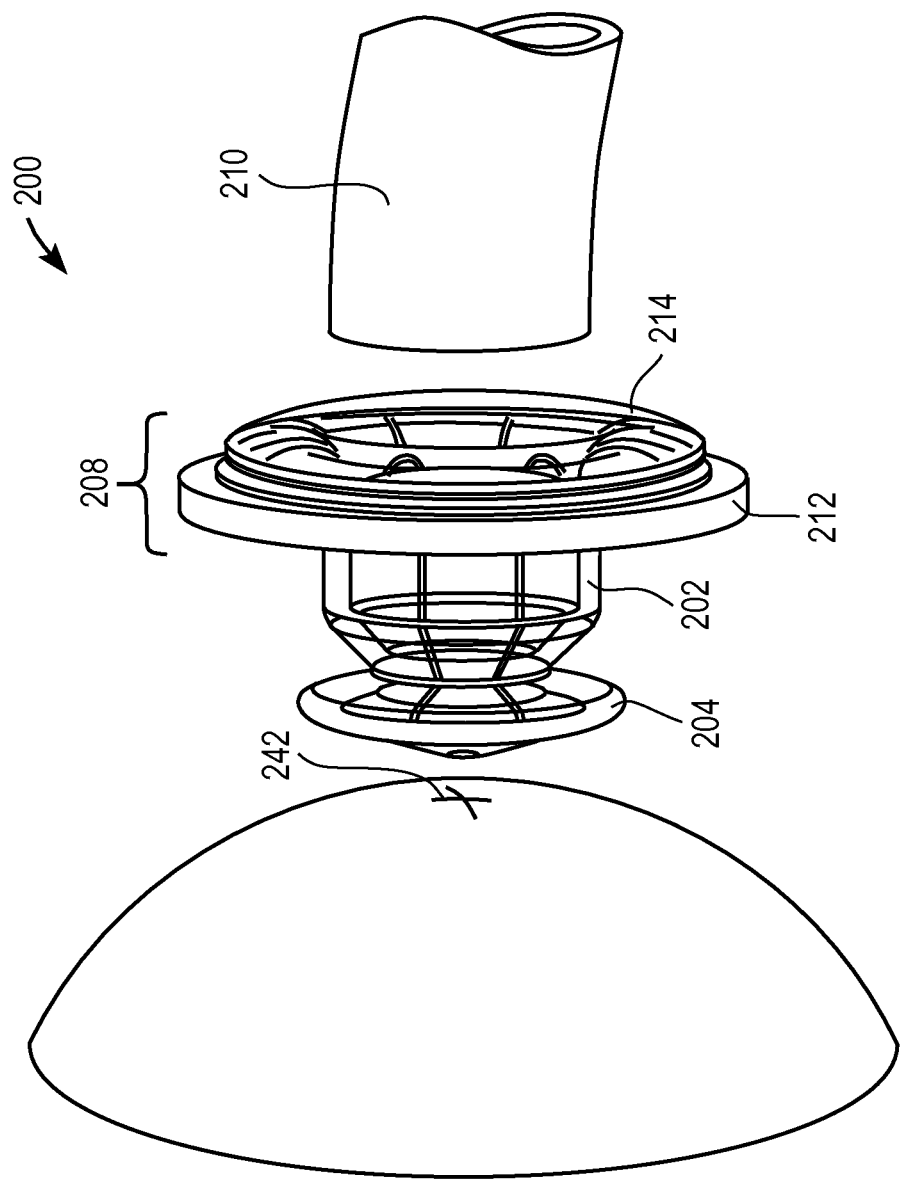
FIG. 16 is a perspective view illustrating a ventricular pump coupling assembly, according to an alternative embodiment of the invention.

FIG. 16 illustrates a ventricular pump coupling 200, according to an alternative embodiment of the invention, including a sleeve 202, a seal member 204, a clamp component 208, and a conduit 210.

The clamp component 208 includes an epicardial seal piece 212 and a flange 214. The flange 214 is formed together with and out of the same components as the sleeve 202 and the seal member 204. The epicardial seal piece 212 is then positioned over the seal member 204 and subsequently over the sleeve 202 until it contacts the flange 214.

Figure 17:
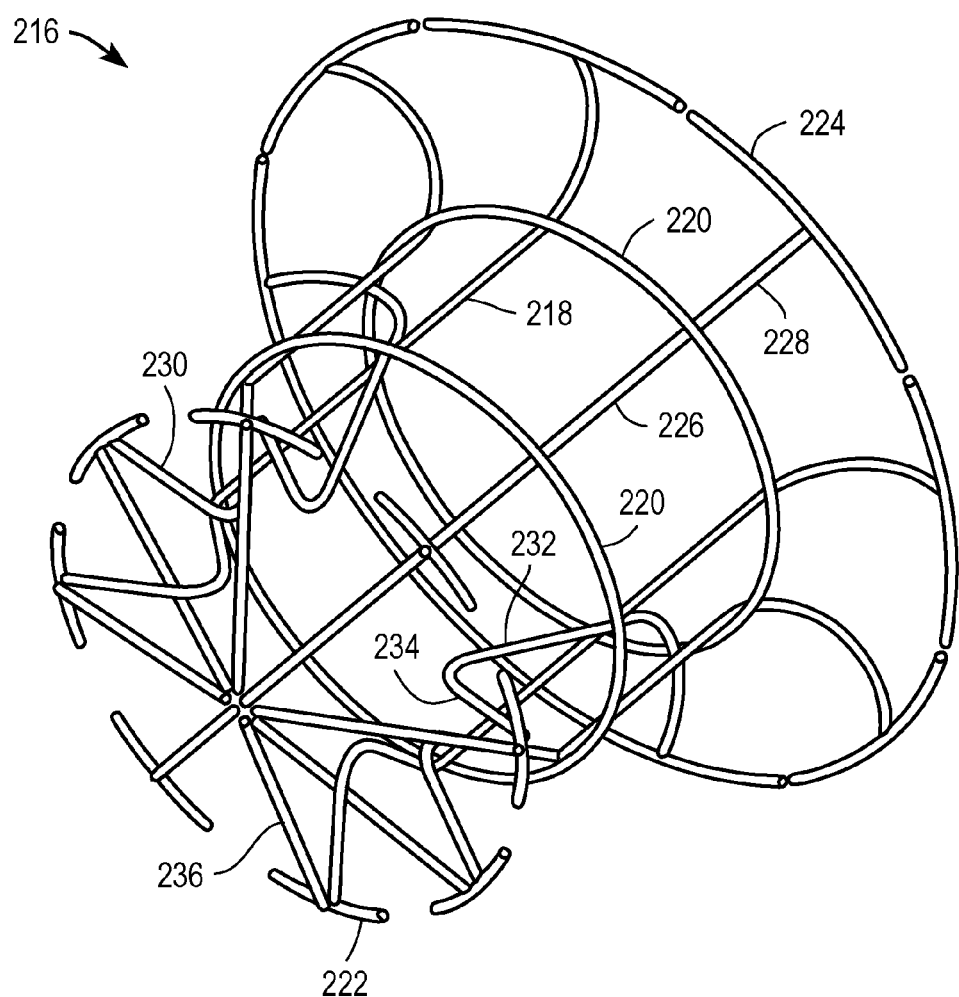
FIG. 17 is a perspective view illustrating a wire frame forming part of the coupling of FIG. 16.

FIG. 17 illustrates a wire frame 216 forming part of the seal member 204, sleeve 202, and flange 214 shown in FIG. 16. The wire frame 216 includes a plurality (in this embodiment eight) of generally axially extending pieces 218, a plurality (in this embodiment two) of support rings 220, a plurality (in number, corresponding to the number of axially extending pieces 218) of distal clamping pieces 222, and a plurality (in number, equaling the number of axially extending pieces 218) of proximal clamping pieces 224. Each one of the axially extending pieces 218 is secured to both of the support rings 220, and the distal and proximal clamping pieces 222 and 224 are secured to the axially extending pieces 218.

Each axially extending piece 218 is bent to have a respective sleeve piece 226, a respective flange piece 228, and a respective seal member piece 230. The seal member piece 230 has sections 232, 234, and 236. The section 232 extends toward a center line of the wire frame 216, the section 234 extends away from the center line, and the section 236 again extends toward the center line. Tips of the sections 236 almost contact one another.

The distal clamping pieces 222 are secured at a location where the sections 234 and 236 meet. Although separated from one another, the distal clamping pieces 222 form a broken circle with a diameter that is only slightly larger than a diameter of one of the supporting rings 220.

The proximal clamping pieces 224 are attached to ends of the flange pieces 228. The flange pieces 228 are curved outwardly, and the proximal clamping pieces 224 form a broken circle having a diameter that is much larger than a diameter formed by the distal clamping pieces 222.

The wire frame 216 is typically made of stainless steel or another metal that is sufficiently rigid, but can be elastically or plastically deformed.

The wire frame 216 is subsequently covered with a thin layer of silicone or other flexible and biocompatible material. The material typically has a thickness of between 0.2 and 1.0 mm. A portion of the material, together with the flange pieces 228 and proximal clamping pieces 224, form the flange 214 shown in FIG. 16. Another portion of the material and the sleeve pieces 226 form the sleeve 202 shown in FIG. 16. Another portion of the material together with the seal member pieces 230 form the seal member 204 shown in FIG. 16. The material forms only a small opening at tips of the sections 236 shown in FIG. 17.

Referring again specifically to FIG. 16, an incision 242 is formed in a wall of a heart, as was explained with reference to FIG. 10. The incision 242 is sufficiently large to allow for the seal member 204 and the sleeve 202 to be inserted into the heart. The epicardial seal piece 212 then contacts the outer wall of the heart. The conduit 210 is then inserted into the sleeve 202.

Figure 18:
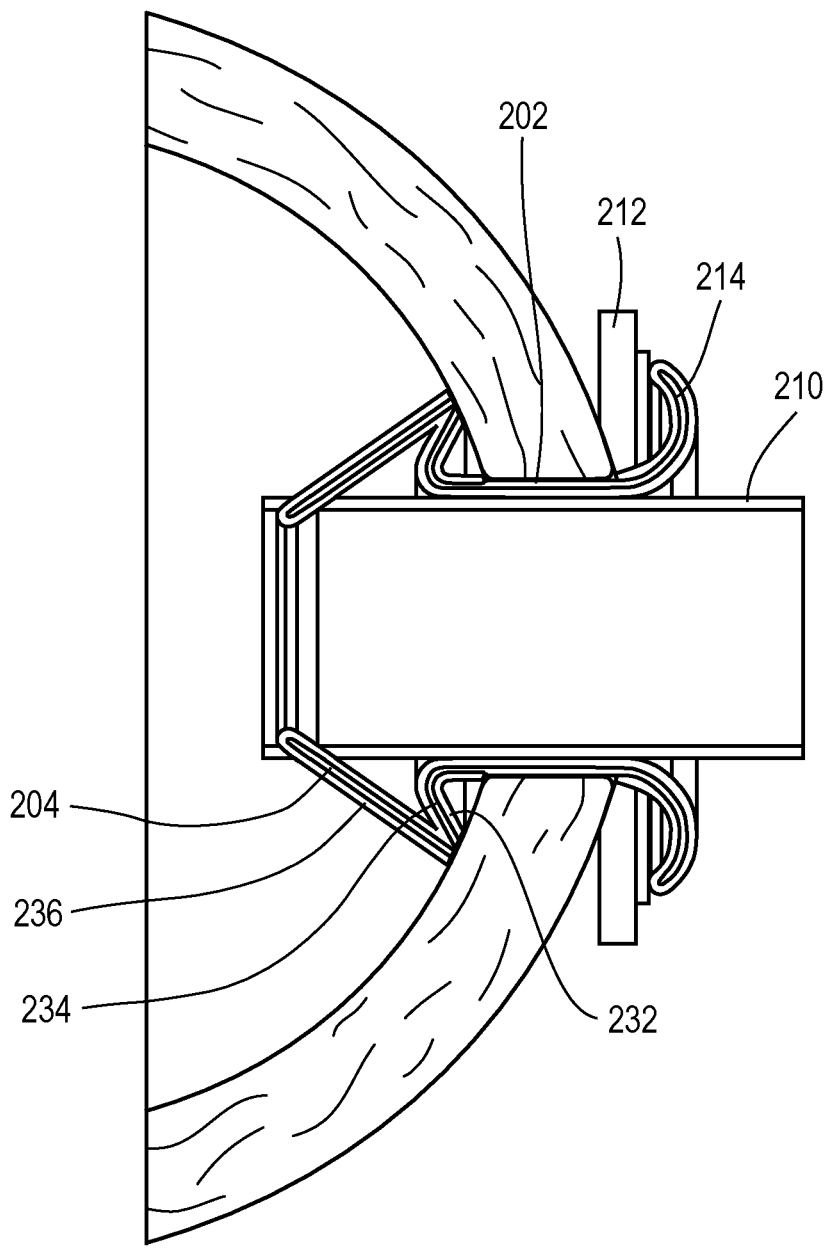
FIG. 18 illustrates how the coupling attaches to a wall of a heart.

FIG. 18 illustrates movement of the seal member 204 after further insertion of the conduit 210. An outer diameter of the conduit 210 is larger than an opening provided by the sections 232. Movement of the conduit 210 to the left relative to the sleeve 202 moves the sections 232 out of the way so that they provide a larger opening for the conduit 210. The sections 234 and 236 rotate together with the sections 232 away from a center line of the conduit 210. The sections 234 rotate into contact with an inner surface of the wall of the heart. There is thus relative movement between the sections 234 and the flange 214 toward one another. The movement of the sections 234 toward the flange 214 enlarges a diameter of the seal member 204 and clamps the wall of the heart between the seal member 204 and the flange 214. Because the sections 236 rotate away from a center line of the conduit 210, the opening provided between tips of the sections 236 enlarges, to allow for blood to flow therethrough. Suturing can be provided to further secure the epicardial seal piece 212 to the wall of the heart.

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed is:

1. A device for creating a sealed connection between an end of a conduit and an opening in a wall of a heart, comprising:
   a sleeve having a first end and second end, the end of the conduit being insertable into the first end of the sleeve and a surface of the conduit sealing with a surface of the sleeve;
   a seal member attached to the first end of the sleeve and capable of moving between a folded position and an open position to expand the seal member so that the seal member has a cross-dimension that is larger than a cross-dimension of the opening in the wall of the heart, the seal member including a first section extending from the sleeve towards a center line of the sleeve and being rotated away from the center line upon further insertion of the conduit into the sleeve, a second section extending from the first section away from the center line and rotating with the first section away from the center line upon insertion of the conduit into the sleeve, and a clamping piece extending distally on the second section when in the folded position and rotating therewith away from the center line and into contact with the wall of the heart upon insertion of the conduit into the sleeve; and
   a clamp component to be positioned outside of the heart, the clamping piece of the seal member and the clamp component being movable relative to one another to produce an axial clamping force with the wall of the heart between the clamp component and the seal member so that a seal is created between the seal member and the wall of the heart.

2. A device as claimed in claim 1, wherein the seal member has a third section extending from the second section towards the center line when in the folded position to penetrate through the wall of the heart.

3. A device as claimed in claim 1, wherein the clamp component is secured to the sleeve and the relative movement is created by rotation of the clamping piece away from the center line.

4. A device as claimed in claim 1, wherein the seal member is molded silicone having a biocompatible coating.

5. A device as claimed in claim 1, further comprising a wire frame, plastic deformation of at least a portion of the wire frame causing expansion of the seal member.

6. A device as claimed in claim 5, wherein movement of the conduit relative to the wire frame causes deformation of the portion of the wire frame.

7. A device as claimed in claim 1, wherein the clamp component has an epicardial seal piece having an inner and outer diameter to engage the wall of the heart.

8. A device as claimed in claim 7, wherein the clamp component has a flange being attached to the epicardial seal piece.

9. A system for assisting a left ventricle of a heart, comprising:
   a conduit with an end;
   a device for creating a sealed connection between the conduit and a wall of the heart, the device including a sleeve having a first end and second end, the end of the conduit being insertable into the first end of the sleeve and a surface of the conduit sealing with a surface of the sleeve, a seal member attached to the first end of the sleeve and capable of moving between a folded position and an open position to expand the seal member so that the seal member has a cross-dimension that is larger than a cross-dimension of the opening in the wall of the heart, the seal member including a first section extending from the sleeve towards a center line of the sleeve and being rotated away from the center line upon further insertion of the conduit into the sleeve, a second section extending from the first section away from the center line and rotating with the first section away from the center line upon insertion of the conduit into the sleeve, and a clamping piece extending distally on the second section when in the folded position and rotating therewith away from the center line and into contact with the wall of the heart upon insertion of the conduit into the sleeve, and a clamp component to be positioned outside of the heart, the clamping piece of the seal member and the clamp component being movable relative to one another to produce an axial clamping force with the wall of the heart between the clamp component and the seal member so that a seal is created between the seal member and the wall of the heart;
   a pump having an outlet and an inlet, the inlet being connected to the conduit;
   a motor for driving the pump;
   an energy source for operating the motor; and
   an outflow tube having a first end and a second end, wherein the first end is connected to the outlet of the pump and the second end is connectable to a blood vessel.

10. A system as claimed in claim 9, wherein the clamp component is secured to the sleeve and the relative movement is created by rotation of the clamping piece away from the center line.

* * * * *